Figure 1B:
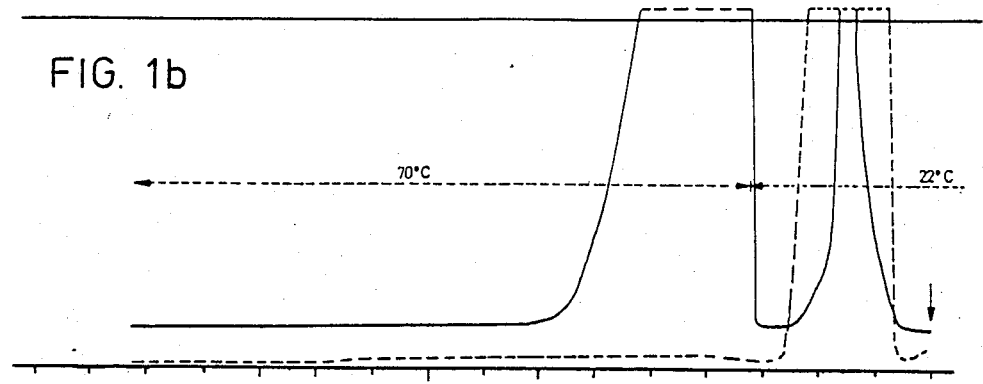

United States Patent [19]

Rauenbusch

[11] Patent Number: 4,904,769

[45] Date of Patent: Feb. 27, 1990

[54] HIGHLY PURE ACARBOSE

[75] Inventor: Erich Rauenbusch, Wuppertal, Fed. Rep. of Germany

[73] Assignee: Bayer Aktiengesellschaft, Leverkusen, Fed. Rep. of Germany

[21] Appl. No.: 940,713

[22] Filed: Dec. 11, 1986

[30] Foreign Application Priority Data

Dec. 13, 1985 [DE] Fed. Rep. of Germany ....... 3543999

[51] Int. Cl.$^4$ .......................... C07H 3/08; A61K 31/70
[52] U.S. Cl. .................................... 536/17.2
[58] Field of Search ...................... 536/127, 55.3, 18.7, 536/25, 17.2; 514/23, 54

[56] References Cited

U.S. PATENT DOCUMENTS

| | | | |
|---|---|---|---|
| 4,062,950 | 12/1977 | Frommer | 536/18.7 |
| 4,174,439 | 11/1979 | Rauenbusch | 536/55.3 |
| 4,526,784 | 7/1985 | Heiker | 536/18.5 |
| 4,536,493 | 8/1985 | Junge | 536/17.9 |
| 4,666,776 | 6/1987 | Lange | 528/304 |

*Primary Examiner*—Ronald W. Griffin
*Attorney, Agent, or Firm*—Sprung, Horn, Kramer & Woods

[57] ABSTRACT

A purified acarbose which contains less than 10% by weight of sugar-like secondary components is obtained by column chromatograph of a solution of prepurified acarbose with a pH 4 to 7. The column contains as a packing material a weakly acid cation exchanger which has carboxyl groups and is based on dextran, agarose and cellulose or exchangers which are derived from the latter with the addition of polyamide.

11 Claims, 1 Drawing Sheet

HIGHLY PURE ACARBOSE

The invention relates to highly pure acarbose, to a process for its preparation and to its use in and for the preparation of medicaments.

Acarbose is an inhibitor of the saccharase enzyme complex of the human small intestine and is used in medicine for the treatment of diabetes.

Acarbose is O-4,6-didesoxy-4-[(1S,4R,5S,6S)-4,5,6-trihydroxy-3-(hydroxymethyl)-2-cyclohexen-1-yl amino]-α-D-glucopyranosyl-(1→4)-O-α-D-glucopyranosyl(1→4)-D-glucopyranose.

The inhibitor is obtained by fermentation of Actinoplanes species (see German Patent Specification 2,209,832, German Patent Specification 2,209,834, German Patent Specification 2,064,092) and has to be isolated from the fermentation broth. Purification processes have been described for this purpose (see German Patent Specification 2,347,782 and German Patent Specification 2,719,912).

In these purification processes, the acarbose is bound to strongly acid cation exchangers and is eluted with salt solutions or, mainly, with dilute acid. The acarbose obtained after neutralization with anion exchangers has a content of 78–88% of acarbose in the dry matter (HPLC method). These preparations still contain impurities in the form of about 10–15% of secondary components giving color reactions for sugars, 1–4% of ash and some coloring constituents. Even higher degrees of purity are necessary for use in human medicine, but, with knowledge of the abovementioned state of the art, these cannot be achieved simply by replacing the strongly acid cation exchangers by weakly acid cation exchangers, since the latter exchangers do not bind the very weakly basic acarbose adequately and it emerges unpurified in the effluent.

It has now been found, surprisingly, that acarbose which has been prepurified in accordance with the state of the art can, after all, be purified, in one step, from residual salts, coloring matter and the sugar-containing basic secondary components on very particular weakly acid hydrophilic cation exchangers in narrowly restricted pH ranges. The content of acarbose after this increases to at least 90% by weight, preferably to 95–98% by weight and more, the sulphated ash decreases to 0–0.5%, and the sugar-like secondary components diminish to less than 10% by weight, preferably 2–5% by weight and less.

Hence the invention relates to acarbose containing less than 10% by weight of sugar-like secondary components.

Acarbose containing 2 to 5% by weight of sugar-like secondary components is preferred, and the invention particularly preferably relates to acarbose containing less than 2% by weight of sugar-like secondary components.

For the preparation of the acarbose according to the invention using this specific type of chromatography, use is made of a solution of prepurified acarbose obtained by, for example, the process which has been described in German Patent Specification 2,719,912. This solution is applied to a column in a concentration of 1–20% and at a pH of 3.5–6.5, preferably 4.0–5.5. Suitable as packing are weakly acid cation exchangers which have carboxyl groups and are based on dextran, agarose and cellulose, or exchangers derived from these components with the addition of polyacrylamides, such as, for example, the commercially available types CM-Sephadex ®, CM-Sepharose ®, CM-Cellulose ®, CM-Cellufine ®, inter alia. Remarkably, the commercially available weakly acid exchangers which contain carboxyl groups and are based on polystyrene, polyacrylic acid or polymethacrylic acid cannot be used for this purification.

Accordingly, the invention furthermore relates to a process for the preparation of acarbose which contains less than 10% by weight of sugar-like secondary components, which is characterized in that prepurified acarbose in a 1 to 20% by weight aqueous solution with a pH of 4 to 7 is applied to a column which contains as packing material weakly acid cation exchangers which have carboxyl groups and are based on dextran, agarose and cellulose or exchangers which are derived from the latter with the addition of polyamide, the column is eluted exclusively with degassed, distilled water and, where appropriate, the acarbose is isolated from the eluate in customary manner.

The volume of the aqueous solution of prepurified acarbose which is applied to the column is restricted. The maximum volume which can be applied corresponds to the filling volume of the column, and preferably less than 60% of the column volume is applied. For this reason, in order to purify a preparative amount of acarbose, the concentrations used are not too low. The concentration is limited in the upward direction by the fact that the ion exchangers best suited for the purification are prone to shrinkage. Concentrations of 7–20% are preferred.

After the application, the column is eluted exclusively with degassed, distilled water. During this there is elution first of salts, neutral sugars and coloring concomitants, and subsequently, more slowly, the acarbose in a relatively broad peak. The sugar-like basic secondary components remain on the column and are not removed until it is regenerated. Thus the acarbose is in the form of a purely aqueous solution at a pH of 6–7 and can be concentrated in a customary manner and dried in a highly pure form.

The behaviour of acarbose on the column depends on several factors of which, surprisingly, those crucial for the practical procedure are the pH of equilibration of the column packing and the temperature during the chromatography.

Alteration of the pH of the column packing alters the capacity and the elution behaviour of acarbose. At neutral pH values, the slowing of acarbose compared with the salts is insufficient, and separation is inadequate. At acid pH values around 3.5–4, the acarbose is greatly slowed down and is only incompletely eluted with water. Carrying out the process in practice requires an optimization of the pH for each particular exchanger. In generaly, pH values between 4.3 and 5.0 are suitable. The pH values which are to be preferred are around 4.6 with high loading and around 4.9 with low loading and maximum yield.

The second important factor is the temperature. The lower the temperature the more strongly acarbose is held back by the ion exchanger, but the greater the capacity of the column the slower the elution of acarbose. This means that an asymmetric peak is obtained and the volume of the acarbose fraction is very large. Hence it is expedient to apply the substance at, or even below, room temperature, and, after the elution of the salts and colouring constituents, to heat the column to about 25° to 90° C., preferably to 40°-70° C. This results ih rapid elution of the acarbose with good yields.

Buffers are used for the regeneration of the ion exchanger, for example sodium acetate buffer in the pH range necessary for the equilibration and in a concentration of 0.1 to 0.5M. Thereafter, the column is washed with pure, degassed water until the conductivity has fallen to about 0.1 mS/cm (room temperature).

In the depictions of the separations, the time is plotted on the abscissa in hours against the refractive index of the eluate and its conductivity (broken line). In addition, the temperature marking is indicated.

The content of acarbose in the final product was determined, in particular, by liquid chromatography (HPLC method) and related to the anhydrous substance.

| The method was carried out as follows: | |
|---|---|
| | High-pressure liquid chromatograph with thermostated column oven, Stainless steel metal column Length: 25 cm internal diameter: 4 mm packed with: aminophase 5 μm (for example LiChrosorb NH$_2$, E. Merck, or Hypersil APS, Shandon) |
| Reagents | 1. Acetonitrile (for example LiChrosolv, E. Merck) 2. Potassium dihydrogen phosphate, analytical grade 3. Disodium hydrogen phosphate dihydrate, analytical grade |
| Test solution | Dissolve about 200 mg of substance, accurately weighed, in a graduated flask and make up to 10.0 ml with water. 20 mg/ml |
| Comparison solution | Dissolve the contents of one ampoule of standard substance in the volume of water indicated for the standard. |
| Eluent | Acetonitrile/phosphate buffer (71 + 29, volumes), Phosphate buffer: dissolve 600 mg of potassium dihydrogen phosphate and 350 mg of disodium hydrogen phosphate-dihydrate and make up to 1000 ml with water. Filter the solution through a 0.8 μm type AAWP Millipore filter. |
| Flow rate | 2.2 ml/min. |
| Temperature of the column oven | 35° C. |
| Detection | UV, 210 nm |
| Amount injected | 10 μl, 0.2 mg in 10 μl |
| Full-scale deflection of recorder | About 0.25 AUFS (absorbance units full scale) |
| Calculation of the acarbose content | $G = \dfrac{P_p \times C \times 100{,}000}{P_v \times E_p \times (100 - b)}$ |
| | G = Content of acarbose in percent, calculated on the basis of the anhydrous substance |
| | P$_p$ = acarbose peak area from the test solution |
| | P$_v$ = acarbose peak area from the comparison solution (standard) |
| | W$_p$ = weight of the sample in mg |
| | C = concentration of the comparison solution in mg of acarbose per ml |
| | b = water content of the |

| -continued | |
|---|---|
| The method was carried out as follows: | |
| | sample in percent |

The inhibitory action of acarbose was determined in the saccharase inhibition assay and reported in saccharase inhibition assay and reported in saccharase inhibition units (SIU). The assay is described by L. Müller, B. Junge et al. in Enzyme Inhibitors, U. Brodbeck ed., Verlag Chemie, 1980, page 109.

The present invention includes pharmaceutical preparations which in addition to non-toxic, inert pharmaceutically suitable excipients contain the active compound according to the invention or which consist of the active compound according to the invention and processes for the production of these preparations.

The present invention also includes pharmaceutical preparations in dosage units. This means that the preparations are in the form of individual parts, for example tablets, dragees, capsules, pills, suppositories and ampoules, of which the content of active substance corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half or a third or a quarter of a daily dose.

By non-toxic, inert pharmaceutically suitable excipients there are to be understood solid, semi-solid or liquid diluents, fillers and formulation auxiliaries of all kinds.

Tablets, dragees, capsules, pills, granules, suppositories, solutions, suspensions and emulsions, pastes, ointments, gels, creams, lotions, powders and sprays may be mentioned as preferred pharmaceutical preparations.

Tablets, dragees, capsules, pills and granules can contain the active compound or compounds alongside the customary excipients such as (a) fillers and extenders, for example starches, lactose, sucrose, glucose, mannitol and silica, (b) binders, for example carboxymethylcellulose, alginates, gelatine and·polyvinylpyrrolidone, (c) humectants, for example glycerine, (d) disintegrating agents, for example agar-agar, calcium carbonate and sodium bicarbonate, (e) solution retarders, for example paraffin, and (f) resorption accelerators, for example quaternary ammonium compounds, (g) wetting agents, for example cetyl alcohol or glycerine monostearate, (b) adsorbents, for example kaolin and bentonite, and (i) lubricants, for example talc, calcium stearate and magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound only, or preferentially, in a certain part of the intestinal tract, optionally in a delayed manner, examples of embedding compositions which can be used being polymeric substances and waxes.

The active compound or compounds, optionally together with one or more of the abovementioned excipients, can also be in a micro-encapsulated form.

Suppositories can contain, in addition to the active compound, the customary water-soluble or water-insoluble excipients, for example polyethylene glycols, fats, for example cacao fat, and higher esters (for example $C_{14}$-alcohol with $C_{16}$-fatty acid) or mixtures of these substances.

Ointments, pastes, creams and gels can contain the customary excipients in addition to the active and eucalyptus oil, and sweeteners, for example saccharin.

The therapeutically active compounds should preferably be present in the abovementioned pharmaceutical preparations in a concentration of about 0.1 to 99.5, preferably of about 0.5 to 95, percent by weight of the total mixture.

The abovementioned pharmaceutical preparations are manufactured in the usual manner according to known methods, for example by mixing the active compound or the active compounds with the excipient or excipients.

The present invention also includes the use of the active compound according to the invention and of pharmaceutical preparations which contain the active compound according to the invention in human and veterinary medicine for the prevention, amelioration and/or cure of illnesses.

The active compound or its pharmaceutical preparations can be administered locally, orally, parenterally, intraperitoneally and/or rectally, preferably parenterally, especially intravenously.

In general it has proved advantageous both in human medicine and in veterinary medicine to administer the active compound in total amounts of about 1 to about 40, preferably 2 to 8, mg/kg of body weight every 24 hours, optionally in the form of several individual administrations, in order to achieve the desired results. An individual administration contains the active compound preferably in amounts of about 0.1 to about 4, especially of 0.2 to 2, mg/kg of body weight. However, it can be necessary to deviate from the dosages mentioned and in particular to do so as a function of the nature and body weight of the subject to be treated, the nature and the severity of the illness, the nature of the preparation and if the administration of the medicine, and the time or interval over which the administration takes place. Thus it can suffice in some cases to manage with less that the abovementioned amount of active compound whilst in other cases the abovementioned amount of active compound must be exceeded. The particular required optimum dosage and the type of administration of the active compound can easily be decided by anyone skilled in the art, on the basis of his expert knowledge.

EXAMPLE 1

Figure 1A:
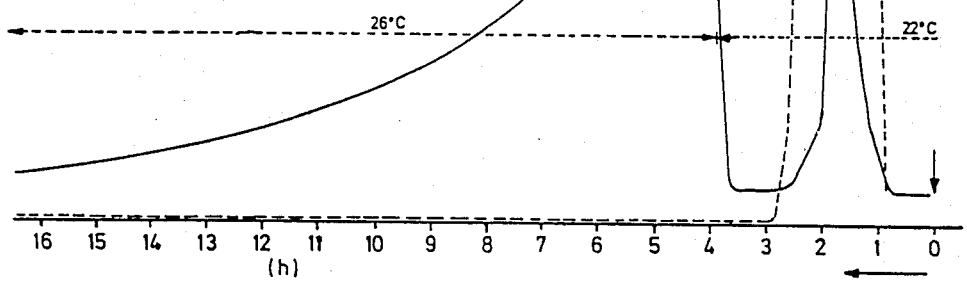

A chromatography column of diameter 2.6 cm and length 40 cm (Pharmacia K 26/40) was packed with CM-Sephadex ® C 25. The CM-Sephadex ® C 25 had previously been equilibrated in 0.2M sodium acetate buffer pH 4.7. After the column had been packed it was washed with distilled, degassed water until the conductivity had fallen to 0.1 mS/cm. The height of the packing in the column was then 34 cm. The test substance used was 5.2 g of prepurified acarbose which, in addition to water, also contained salts and other impurities. The acarbose was dissolved in about 40 ml of distilled water, the pH was adjusted to 4.7 by addition of a little hydrochloric acid, and the solution was made up to 50 ml. The inhibitor content was 446,550 SIU, corresponding to 5.75 g of pure anhydrous acarbose. The substance was applied at a flow rate of 100 ml/h (18.8 cm/h) to the column and was washed and eluted with distilled water at 26° C. The course of the separation is shown in FIG. 1a. The main fraction was combined and resulted in a yield of 5.87 g containing 399,300 SIU, which is 89% of the inhibitor employed. The specific activity was 72 SIU/mg of dry matter. The HPLC method showed a content of 93% in the dry matter.

The column was regenerated with 800 ml of 0.2M sodium acetate buffer, pH 4.7, and the latter was subsequently washed out with 600 ml of distilled, degassed water.

EXAMPLES 2-5

All the examples in Table 1 were carried out in accordance with Example 1, but the temperature of the column jacket was varied during the elution. The elution was such that, three hours after the start of the application, the thermostat of the column heating was switched on and reached, depending on the temperature set, the target figure in 3–12 minutes. The decrease in the volume of the main fraction is indicated in Table 1, and Example 5 with an elution temperature of 70° C. is in FIG. 1b.

TABLE 1

Chromatography of acarbose on CM-Sephadex ® C 25
Dependence of the elution volume on the temperature

| Example | Temperature of elution °C. | Volume of main fraction ml | yield g | yield % | Content by HPLC % |
|---|---|---|---|---|---|
| 1 | 26 | 1,163 | 5.87 | 89 | 95 |
| 2 | 40 | 840 | 6.25 | 100 | 92 |
| 3 | 50 | 570 | 6.04 | 91 | 90 |
| 4 | 60 | 460 | 5.92 | 86 | 92 |
| 5 | 70 | 380 | 6.62 | 99 | 94 |

EXAMPLE 6

A chromatography column (Pharmacia K 26/70) was packed as in Example 1 with CM-Sephadex ® C 25 which had, however, been equilibrated and washed at pH 4.3. The height of the packing was 47 cm. The test substance used was again, as in Example 1, a prepurified acarbose, 579,000 SIU being applied in 200 ml of water. The flow rate was 117 ml/h (22 cm/h). The elution was carried out with water; as in Example 1, there was elution first of salt-containing fractions and subsequently of acarbose. The gap between the end of the salt-containing fractions and the start of the rise for acarbose was 162 ml. The rate of elution of acarbose was increased by heating the column to 45° C. the volume of the acarbose fraction was 1048 ml, and the yield was 577,000 SIU, which is 100% of the amount applied.

EXAMPLE 7

As in Example 6, a chromatography column was packed with CM-Sephadex ® C 25 which had, however, been equilibrated and washed at pH 4.9. 200 ml of the test solution containing 579,000 SIU were applied, and the substances were eluted with water. The gap between the salt-containing fractions and the start of the acarbose fraction was now only 23 ml. The volume of the main fraction was 707 ml, the temperature again being increased to 45° C. The yield was 577,000 SIU, which is 100% of the amount applied.

EXAMPLE 8

A chromatography column (Pharmacia K 26/40) was packed with CM-Sepharose ® Cl 6B fast flow, equilibrated at pH 4.5 with 0.2M sodium acetate solution and washed with water. 40.5 ml of a solution of prepurified acarbose with an inhibitory action of 247,300 SIU were applied. The flow rate was 100 ml/h (18.8 cm/h). The elution was carried out with degassed, distilled water, the column having been heated to 45° C. at the start of the acarbose elution. The gap between the salt fraction and the acarbose fraction was 38 ml, and the volume of the main fraction was 600 ml. The yield of acarbose was 247,000 SIU, which is 100% of the amount used. The content by the HPLC method was 98% in the dry matter.

EXAMPLE 9

A chromatography column as in Example 8 was packed with carboxymethylcellulose CM 52 ® (Whatman), equilibrated to pH 4.5 with 0.2M sodium acetate solution, and washed with water. The height of the packing was 36 cm. 62 ml of a solution of prepurified acarbose with an inhibitory action of 394,000 SIU were applied, and eluted as in Example 8. The acarbose fraction followed immediately after the salt fraction. The volume of the acarbose fraction was 850 ml, and the yield was 322,000 SIU, which is 82% of the amount used. Content by the HPLC method 90% in the dry matter.

EXAMPLE 10

A chromatography column as in Example 8 was packed with Matrex-Cellufine CM ® (Amicon), equilibrated to pH 4.5 with 0.2M sodium acetate solution, and washed with water. The height of the packing was 37 cm. 62 ml of a solution of prepurified acarbose with an inhibitory action of 394,000 SIU were applied, and eluted as in Example 8. The acarbose fraction followed the salt fraction after a gap of 23 ml. The volume of the acarbose fraction was 960 ml, and the yield was 350,000 SIU, which is 89% of the amount applied. Content by the HPLC method 98% in the dry matter.

What is claimed is:

1. A purified acarbose composition which, apart from water, has an acarbose content of about 93–98% by weight.

2. An acarbose composition according to claim 1, which, apart from water, contains 2 to 5% by weight of sugar-like secondary components.

3. An acarbose composition according to claim 1, which, apart from water, contains less than 2% by weight of sugar-like secondary components.

4. A process for the preparation of a purified acarbose composition according to claim 1, comprising applying a prepurified acarbose in a 1 to 20% by weight aqueous solution with a pH of 3.5 to 7 to a column which contains as packing material a weekly acid cation exchanger which has carboxyl groups and is based on dextran, agarose and cellulose or exchangers which are derived from the latter with the addition of polyamide, eluting the column exclusively with degassed, distilled water and isolating the purified acarbose composition from the eluate.

5. A process according to claim 4, wherein the volume of prepurified acarbose solution which is applied corresponds to the filling volume of the column.

6. A process according to claim 4, wherein the volume of prepurified acarbose solution is less than 60% of the column volume.

7. A process according to claim 4, wherein the pH of the prepurified acarbose solution is 3.5 to 6.0.

8. A process according to claim 4, wherein the pH of the prepurified acarbose solution is 4.0 to 5.5.

9. A process according to claim 4, wherein the prepurified acarbose solution is applied at temperatures up to room temperature, and, the column is heated to 25° to 95° C. after the salts and coloring constituents have been eluted therefrom.

10. A process according to claim 9, wherein the prepurified acarbose solution is applied at temperatures in the range from 4° to 25° C., and, after the salts and coloring constituents have been eluted, the column is heated to 40° to 70° C.

11. A pharmaceutical composition comprising an effective amount of an acarbose composition according to claim 1, said acarbose, apart from water, contains less than 10% by weight of sugar-like secondary components and a pharmaceutically acceptable excipient therefor.

* * * * *

UNITED STATES PATENT AND TRADEMARK OFFICE

CERTIFICATE EXTENDING PATENT TERM
UNDER 35 U.S.C. § 156

PATENT NO.      :  4,904,769

ISSUED          :  February 27, 1990

INVENTOR(S)     :  Erich Rauenbusch

PATENT OWNER    :  Bayer Aktiengesellschaft

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 922 days from the original expiration date of the patent, February 27, 2007, with all rights pertaining thereto as provided by 35 U.S.C. § 156(b).

I have caused the seal of the Patent and Trademark Office to be affixed this 21st day of April 1997.

Bruce A. Lehman
Assistant Secretary of Commerce and
Commissioner of Patents and Trademarks

Disclaimer 4,904,769 — Erich Rauenbusch, Wuppertal, Fed. Rep. of Germany. HIGHLY PURE ACARBOSE. Patent dated Feb. 27, 1990. Disclaimer filed Dec. 20, 2006, by the assignee, Bayer Healthcare AG.

Hereby enters this disclaimer to all claims of said patent.

*(Official Gazette February 27, 2007)*